United States Patent [19]

Skillern

[11] 4,005,198
[45] Jan. 25, 1977

[54] TREATMENT OF ACNE VULGARIS
[75] Inventor: Scott D. Skillern, South Bend, Ind.
[73] Assignee: Robert H. Van Aman, Jupiter, Fla.
[22] Filed: Sept. 12, 1975
[21] Appl. No.: 612,686
[52] U.S. Cl. .............................. 424/227; 424/246
[51] Int. Cl.² .................. A61K 31/65; A61K 31/54
[58] Field of Search ........................... 424/246, 227
[56] References Cited
OTHER PUBLICATIONS Physician's Desk Reference, (PDR), (1971), pp. 505–506.
Hopponen, Handbook of Non-Prescription Drugs, (1973 Edition), pp. 155–160.
Cooper et al, Medical Annals of the District of Columbia, Feb., 1960, pp. 75–76.

Handbook of Pharmacology, Cutting, 4th Edition, pp. 234–237, 288–289.

Primary Examiner—Norman A. Drezin
Attorney, Agent, or Firm—Hal H. McCaghren

[57] ABSTRACT

This invention is directed to the employment of a specific diuretic, methyclothiazide, in minimal dosage of 2.5 to 5.0 mg. per 48 hour period; preferably every other morning in conjunction with a daily dosage of an antibiotic tetracycline, in minimal dosage of 250 mg.daily; and, the unique method of treatment and administering these compounds.

Acne vulgaris is divided into grades. This discovery is for the unique treatment and control of acne vulgaris grades 1, 1½ and usually 2.

2 Claims, No Drawings

TREATMENT OF ACNE VULGARIS

STATE OF THE ART

The past treatment of acne vulgaris has been directed primarily to the step of cleanliness, with multiple washings with soap and water daily; and topical application of various astringents and ointments or salves to prevent spread of inflamed lesions, and in severe cases comedone extractors were used.

In more recent times a theory has developed that acne vulgaris may be caused, at least in part, from comedones formed in the hair follicle, when the internal fatty acids change to free fatty acids in the sebaceous glands or ducts, forming comedones, as well as attracting bacteria causing infection when the pustule forces the comedones out, this frequently results in scarring or scar formation. The use of this new treatment early in the acne development of patients can usually, avoid complications of acne scarring.

Various chemical therapy treatments have been unsuccessfully employed in research efforts to control acne vulgaris by both internal treatment to prevent the formation of a free fatty acid, which itself is a primary irritant of the skin, as well as attracting the bacterial infection; while maintaining the external and topical treatment.

DESCRIPTION OF THE INVENTION

Through clinical tests over the past seven years, which have been accelerated in the past four years in excess of 3,500 cases on clinical report, it has been discovered that a new treatment of Grade 1, 1½ and usually Grade 2 of acne vulgaris, comprises dosage of 5.0 mg. methyclothiazide every other morning with a glass of water or equivalent liquid and 250 mg. tetracycline daily, preferably in the morning, while continuing the external washing treatment; had remarkable results in the control of acne vulgaris in grades 1, 1½ and usually 2.

This new treatment has had remarkable results in the control of acne vulgaris, grades 1, 1½ and 2, in 90–95% of all patients on clinical report over the past four years, on both male and female patients, with equally successful results.

When the patient weighs less than 120 pounds the dosage of methyclothiazide may be started at 2.5 mg. dosage every other morning to avoid any hypotension or diuresis, and after a week to ten days of treatment, they may be placed on the 5.0 mg. dosage every other morning.

To supplement the above, we generally have the patient apply topical applications of benzoyl peroxide gel for the initial 6 weeks. Thereafter, experience has proved that such gel is needed only occasionally. In all instances we instruct the patient to avoid chocolate; and on occasions, when necessary, foods high in iodine content.

Through the use of this entirely new, and specific treatment, our patient visits have been reduced from every 2 weeks, to 3 weeks and rapidly on up to 5 and 6 week intervals, with the continued high percentage of success referred to above.

The present concept accepted by most doctors in the dermotological field is that tetracycline acts in such a way as to lessen the flow or formation of free fatty acids from the sebaceous gland thus helping to improve the acne. This point is made to emphasize that the tetracycline is not used in this treatment because of its antibiotic activity.

After 6 weeks, the tetracycline, in many cases, needs to be used only intermittently, as needed by the patient to control the episodes of acne inflamation described as inflamatory erythema, papular or pustular lesions involving the sebaceous glands.

Through thorough clinical testing, we have determined that methyclothiazide is the only compound that obtains the highly successful results desired, in its action on the sebaceous gland, to control acne as outlined above. Thus, the use of this old drug in minimal dosage that is systemically excretes in 24 hours, accomplishes a new result, when used in this new method of treatment for acne:

What is claimed is:

1. A method for the treatment of acne vulgaris in a patient having acne vulgaris which comprises orally administering methyclothiazide in a dosage of 2.5 to 5.0 mg. bi-daily.

2. A method, as in claim 1, where there is concurrently administered daily 250 mg. of tetracycline.

* * * * *